United States Patent [19]

Wood, Jr.

[11] 4,246,185

[45] Jan. 20, 1981

[54] CATALYST METAL SEPARATION FROM SATURATED ALIPHATIC MONOCARBOXYLIC ACIDS

[75] Inventor: Frank Wood, Jr., Houston, Tex.

[73] Assignee: Celanese Corporation, New York, N.Y.

[21] Appl. No.: 65,240

[22] Filed: Aug. 9, 1979

[51] Int. Cl.³ .................... C07C 51/235; C07C 55/07
[52] U.S. Cl. .................................. 260/413; 562/531; 562/597
[58] Field of Search ............... 252/413; 562/531, 536, 562/549, 597; 260/438.1, 429 R, 413 N; 423/50

[56] References Cited

U.S. PATENT DOCUMENTS

| | | | |
|---|---|---|---|
| 2,828,337 | 3/1958 | Whitaker | 260/413 |
| 3,492,340 | 1/1970 | Aguilo et al. | 252/413 |
| 3,840,469 | 10/1974 | Hobbs, Jr. et al. | 252/413 |
| 4,008,306 | 2/1977 | Yamashita | 423/50 |

FOREIGN PATENT DOCUMENTS 52-33614  3/1977  Japan .

Primary Examiner—P. E. Konopka
Attorney, Agent, or Firm—Linn I. Grim

[57] ABSTRACT

A process is described for separating soluble copper and manganese catalysts from organic saturated aliphatic monocarboxylic acids having 6 to 9 carbon atoms by precipitating the copper and manganese as oxalates into a separate aqueous phase.

12 Claims, 1 Drawing Figure

METAL SEPARATION SYSTEM

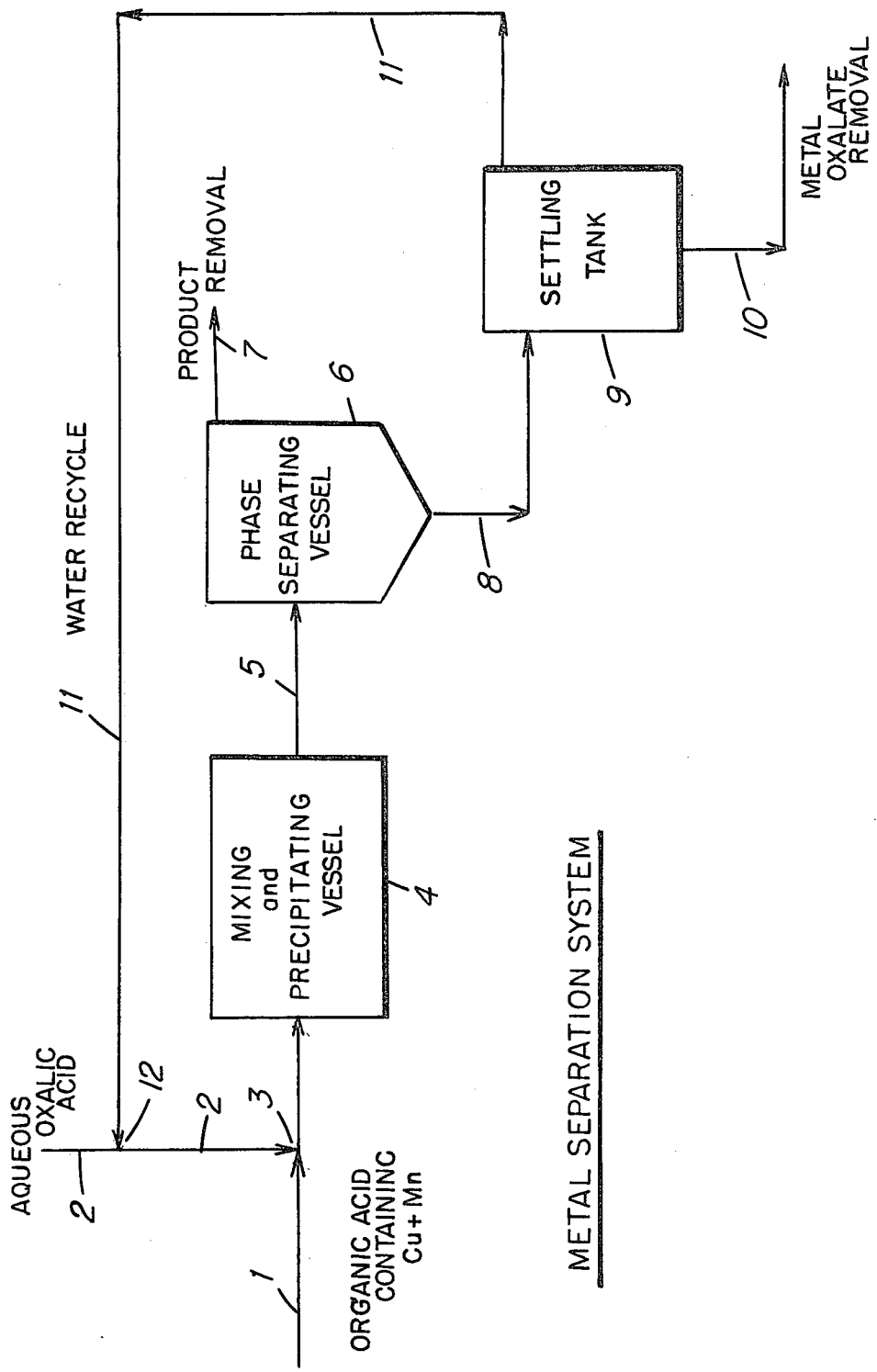

CATALYST METAL SEPARATION FROM SATURATED ALIPHATIC MONOCARBOXYLIC ACIDS

BACKGROUND OF THE INVENTION

In the production of organic saturated aliphatic monocarboxylic acids having 6 to 9 carbon atoms by oxidation of the corresponding aldehydes, soluble manganese and copper compounds, such as manganous acetate and cupric acetate, are used in combination as catalysts to provide high carbon conversion and high efficiency of aldehyde to acid. High carbon conversion and high efficiency essential not only to provide good yields of acids but also to produce relatively small amounts of undesirable by-products and thus avoid recycling unreacted starting materials. The oxidation reaction can be conducted in the liquid phase using a single stage or multiple stage reactors. These reactions can be operated under pressure in the range from about 60 to about 150 pounds per square inch gauge, preferably from about 85 to about 95 pounds per square inch gauge, with air or oxygen containing gas in the temperature range from about 50° C. to about 80° C. Such a process is described in copending application U.S. Ser. No. 065,241 filed Aug. 9, 1979 assigned to the same assignee and filed concurrently with this application.

However, it has been found that metallic copper will precipitate from acids prepared using such mixed soluble catalyst compounds due to reduction during the processing of these acids, especially during distillation. The presence of precipitated copper particles in turn can lead to serious mechanical problems such as reboiler fouling and erosion of pump impellers. Manganese compounds, on the other hand, tend to remain soluble and are not readily reduced to the metal.

Removing the soluble metal catalysts from the acid products would not only avoid the aforementioned mechanical problems but would also provide purer acid products. Copending application U.S. Ser. No. 065,239 filed Aug. 9, 1979, assigned to the same assignee and filed concurrently with this application, describes the precipitation of copper and manganese as oxalates from 3–9 carbon acid products containing them by the addition of oxalic acid thereto. The copper and manganese oxalates can then be filtered from the acid products by normal filtration, using a continuous centrifuge or other separation techniques.

In the prior art, there are various techniques to describe the removal of metal catalysts from the reaction product. In U.S. Pat. No. 3,840,469, there is a disclosure for the cobalt catalyst recovery from an acetic acid medium derived from the liquid phase oxidation of aliphatic hydrocarbons. This procedure precipitates the cobalt as cobalt oxalate in the acetic acid product. The patent indicates that manganese would not undergo precipitation in this procedure. In U.S. Pat. No. 2,380,731, a procedure is described using oxalic acid to remove numerous metals such as iron, magnesium, chromium, copper, vanadium etc. from a refractory inorganic support such as a clay or alumina or silica or an alumina-silica refractory catalytic cracking catalyst. These procedures are not related to the process of this invention.

It is the purpose of this invention to provide an improved procedure for separating soluble manganese and copper catalysts from acid products containing them.

SUMMARY OF THE INVENTION

The present invention is a simple process for separating manganese and copper from organic saturated aliphatic monocarboxylic acids having 6 to 9 carbon atoms. This is accomplished by treating the organic acid containing the soluble metal catalysts with an aqueous solution of oxalic acid for a period of time sufficient to precipitate metallic copper and manganese as their oxalates. Upon the addition of the aqueous oxalic acid solution, two phases form: (1) an organic acid phase substantially insoluble in water and (2) an aqueous phase containing the precipitated copper and manganese oxalates which readily separate from the organic phase into the aqueous phase. At this point, the organic acid phase can be decanted, continuously or batchwise, from the aqueous phase. This acid phase can then be further purified by distillation. This technique avoids the necessity of filtering or centrifuging an organic acid medium containing copper and manganese oxalates.

DETAILED DESCRIPTION OF THE INVENTION

The drawing is a diagrammatic illustration of a metal separation system of the present invention.

Referring to the drawing, a solution of organic aliphatic monocarboxylic acids containing soluble manganese and copper catalysts, for example manganese and copper acetate, is fed through line 1 to mix at point 3 with an aqueous solution of oxalic acid fed through line 2. The mixture of organic acid solution and aqueous oxalic acid solution is then fed to vessel 4 where further mixing and precipitation of manganese and copper oxalates is completed. The mixture containing precipitated copper and manganese oxalates is then fed through line 5 to a phase separation vessel 6 wherein two phases are formed. The top phase is the desired product, the organic acid phase, which is removed from the phase separation unit through line 7. The lower phase in the phase separation unit is an aqueous solution containing precipitated manganese and cupric oxalate. This lower phase is fed through line 8 to a settling tank 9 wherein the manganese and cupric oxalate, being sufficiently heavy to settle to the bottom of the tank 9, can be removed from the system through line 10 and recovered. Water can be recycled through line 11 to line 2 at point 12 for reuse. Sufficient oxalic acid is continuously added to line 2 to continue the separation process as described.

The organic acids subjected to the separation process of this invention are derived from the oxidation of their corresponding aldehydes using catalytic amounts of a mixture of soluble manganese and copper catalyst such as manganous acetate and cupric acetate, which are soluble in the acid product, and will contain from 6 to 9 carbon atoms. These acids include hexanoic, heptanoic, octanoic and nonanoic acids, and are substantially insoluble in water. The unique separation process of the present invention is particularly useful in purifying heptanoic and nonanoic acids, which in turn are useful in the preparation of various esters used as additives in lubricating oils.

As previously stated, when an aqueous solution of oxalic acid is mixed with organic acid containing soluble manganese and copper compounds, insoluble manganous oxalate and cupric oxalate are precipitated from the organic acid phase into the aqueous phase and subsequently settle to the bottom of the aqueous phase. The time required for the organic and aqueous phase to form decreases as the organic acid to water volume ratio decreases. The volume ratio of the organic acid to water can range from about 0.5 to about 5.0 to 1, preferably 1.1 to 2.5 to 1, more preferably 1.1 to 1.7 to 1, at 25° C. Under these conditions, the phasing time can range from about 2 minutes to 30 minutes, with shorter times being preferable. At volume ratios of organic acid to water in excess of 5 to 1, the phasing time is longer than 30 minutes.

The amount of oxalic acid present in the aqueous solution should be sufficient to precipitate most of the manganese and copper from the organic acids. Preferably, at least a stoichiometric amount of oxalic acid to metal catalysts can be used and it is particularly desirable to utilize some excess of oxalic acid over the stoichiometric amount of oxalic acid to metal catalysts, e.g. amount of from as low as 2 to as high as 2 to 100 percent excess and in the range of 300 to 500 percent excess. This excess oxalic acid will not be lost since an aqueous phase recycle can be utilized and substantially no oxalic acid dissolves in the acid product.

It is highly desirable that settling of the metal oxalates in the aqueous phase occurs within a reasonable time so that the water can be recycled, if desired, to the initial separation step. The metal oxalates which have been separated from the aqueous phase can be recovered for their metal content or can be thrown away.

It has been discovered that manganese in the form of $Mn^{+3}$ will not readily precipitate as the oxalate whereas $Mn^{+2}$ is readily precipitated. One technique for reducing $Mn^{+3}$ to $Mn^{+2}$ or maintaining manganese as $Mn^{+2}$ is to blanket the organic acid phase containing manganese with nitrogen, or to sparge the organic acid phase with nitrogen, thereby eliminating the oxygen which causes the formation of the $Mn^{+3}$ ion.

The invention will be illustrated by the following examples.

EXAMPLES 1-6 n-Heptanoic acid produced by the oxidation of n-heptanal in the presence of a catalyst consisting of a combination of copper acetate and manganese acetate (330 parts per million copper and 295 parts per million manganese) was combined at ambient temperature with an excess of oxalic acid to the copper and manganese present (on a mole to mole basis). The oxalic acid was added as an aqueous solution. The volume ratio of heptanoic acid present to the water in the aqueous oxalic acid ranged from 1.7/1 to 9.2/1. Two phases, an organic acid phase and an aqueous phase, formed, the copper and manganese oxalates precipitated from the organic acid phase into the aqueous phase, and the precipitated oxalates subsequently settled. The time required for the organic and aqueous phases to form decreased as the organic acid to water volume ratio decreased. Table I illustrates these results:

TABLE I

Phasing Time at 25° C. of Heptanoic Acid* and Aqueous Oxalic Acid

| | | | Metallic Content in Organic Phase | | |
|---|---|---|---|---|---|
| Examples | Organic Acid: Water Volume Ratio | % Excess of Stoichiometric Amounts of Oxalic Acid to Metals | Copper Parts per Million | Manganese Parts per Million | Initial Phasing Time |
| 1 | 9.2 | 2 | 8.4 | 4.6 | ≧ one hour |
| 2 | 5.0 | −6 | 6.2 | 8.9 | ≧ 0.5 hour |
| 3 | 5.0 | 2 | 6.0 | 7.0 | ≧ 0.5 |
| 4 | 2.5 | 2 | 0.3 | 1.6 | ~ 15 minutes |
| 5 | 1.7 | 2 | 1.1 | 1.5 | ~ 5 minutes |
| 6 | 1.7 | 2 | 0.1 | 1.2 | ~ 3 minutes |

*330 parts per million copper and 295 parts per million manganese in heptanoic acid to be treated

EXAMPLES 7-9

The procedure employed in Examples 1-6 was repeated but the highly preferred conditions shown in Table II were employed.

TABLE II

| Examples | Organic Product | Organic Acid: Water Volume Ratio | % Excess of Stoichiometric Amounts of Oxalic Acid to Metals | Organic Phase Copper % Removal | Mn % Removal | Initial Phasing Time |
|---|---|---|---|---|---|---|
| 7 | heptanoic acid 330 ppm Cu and 295 ppm Mn | 1.7 | 2 | 99.9 | 99.6 | ~3 minutes |
| 8 | heptanoic acid 330 ppm Cu and 295 ppm Mn | 1.7 | 10 | 99.9 | 99.9 | ~3 minutes |
| 9 | nonanoic acid 400 ppm Cu and 360 ppm Mn | 1.7 | 10 | 99.9 | 99.9 | ~2 minutes |

In Examples 7 through 9, the time required for the organic acid and aqueous phases to form has been reduced to a minimum, and substantially all of the metals were removed from the organic acid phase.

What is claimed is:

1. A process for separating manganese and copper from organic saturated aliphatic monocarboxylic acids having 6 to 9 carbon atoms which comprises treating said manganese- and copper-containing organic acids with an aqueous solution of oxalic acid in an amount sufficient to precipitate substantially all of the copper and manganese present as the oxalates from the organic acid phase into the aqueous phase, and decanting said organic acid phase from said aqueous phase.

2. The process of claim 1 wherein the volume ratio of organic acid to water ranges from about 0.5/1 to 5/1.

3. The process of claim 1 wherein the volume ratio of organic acid to water ranges from 2.5 to 1 to 1.1 to 1.

4. The process of claim 3 wherein the volume ratio of organic acid to water ranges from 1.1 to 1.7.

5. The process of claim 4 wherein at least 2% more than the stoichiometric amount of oxalic acid necessary to precipitate the copper and manganese present as the oxalates is used.

6. The process of claim 3 wherein precipitated manganese oxalate and cupric oxalate are separated from said aqueous phase and the water from said aqueous phase is then reused in the separation process.

7. The process of claim 5 wherein the organic saturated aliphatic monocarboxylic acids comprise heptanoic acid.

8. The process of claim 5 wherein the organic saturated aliphatic monocarboxylic acids comprise nonanoic acid.

9. In a process for producing organic saturated aliphatic monocarboxylic acids having 6 to 9 carbon atoms from their corresponding aldehydes by oxidizing said aldehydes in the presence of soluble manganese and copper compounds as catalysts, the improvement which comprises separating manganese and copper from said organic saturated aliphatic monocarboxylic acids by treating said organic acids which an aqueous solution of oxalic acid, the volume ratio of said organic acid to water being in the range from 0.5 to 1 to 5 to 1 and the amount of oxalic acid present being sufficient to precipitate substantially all of the copper and manganese as cupric oxalate and manganese oxalate, respectively, to precipitate said oxalates from said organic acids into the aqueous phase, and decanting said organic acids from said aqueous phase.

10. The process of claim 9 wherein the volume ratio of said organic acids to water ranges from 2.5 to 1 to 1.1 to 1 and at least about 2% more than the stoichiometric amount of oxalic acid necessary to precipitate the copper and manganese present as the oxalates is used.

11. The process of claim 10 wherein said organic acids comprise heptanoic acid.

12. The process of claim 10 wherein said organic acids comprise nonanoic acid.

* * * * *